United States Patent [19]

Kajfez et al.

[11] 3,998,811
[45] Dec. 21, 1976

[54] OPTICALLY ACTIVE 1,4-BENZODIAZEPINES AND PROCESS FOR THE PREPARATION THEREOF

[75] Inventors: Franjo Kajfez; Nikola Blazevic; Vitomir Sunjic, all of Chiasso, Switzerland

[73] Assignee: CRC Compagnia di Recerca Chimica S.A., Chiasso, Switzerland

[22] Filed: July 30, 1974

[21] Appl. No.: 493,145

Related U.S. Application Data

[63] Continuation-in-part of Ser. No. 234,645, March 14, 1972, abandoned.

[30] Foreign Application Priority Data

Mar. 17, 1971 Switzerland .................. 3868/71

[52] U.S. Cl. .................. 260/239.3 D; 260/562 N; 424/244; 424/274; 260/326.14 R
[51] Int. Cl.² .................................. C07D 243/24
[58] Field of Search ................... C07D/243/28; 260/239.3 D

[56] References Cited

UNITED STATES PATENTS 3,371,085  2/1968  Reeder et al. ............... 260/239.3 D

FOREIGN PATENTS OR APPLICATIONS 44-26302  11/1969  Japan .................. 260/239.3 D

OTHER PUBLICATIONS

Sternbach et al. "J. Org. Chem." vol. 27, pp. 3788-3796 (1962).

*Primary Examiner*—Henry R. Jiles
*Assistant Examiner*—Robert T. Bond
*Attorney, Agent, or Firm*—Haseltine, Lake & Waters

[57] ABSTRACT

Optically active compounds having the formula

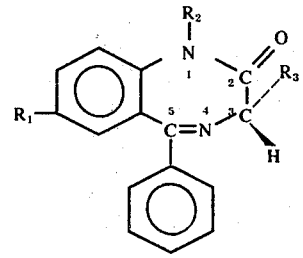

having an asymmetric carbon atom in position 3 having the S configuration and wherein $R_1$ is selected from the class consisting of hydrogen, halogen, nitro, and trifluoromethyl groups, $R_2$ is selected from the group consisting of hydrogen and $C_{1-4}$ lower alkyl groups and $R_3$ is selected from the group consisting of $C_{1-4}$ lower alkyl, hydroxy $C_{1-4}$ lower alkyl, phenyl, hydroxy phenyl, benzyl, hydroxy benzyl, and 3'-methyleneindolyl groups.

They are obtained by reaction of a compound having the formula

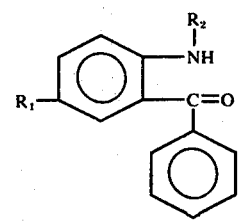

with a compound of the formula

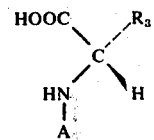

wherein A is a protective group.

The compounds of formula I have sedative and tranquilizing properties.

15 Claims, No Drawings

OPTICALLY ACTIVE 1,4-BENZODIAZEPINES AND PROCESS FOR THE PREPARATION THEREOF

This application is a continuation-in-part of our copending application Ser. No. 234,645, filed Mar. 14, 1972, and entitled "Optically Active 1,4-Benzodiazepines and Process for the Preparation Thereof, now abandoned."

BACKGROUND OF THE INVENTION

Compounds similar to those of formula

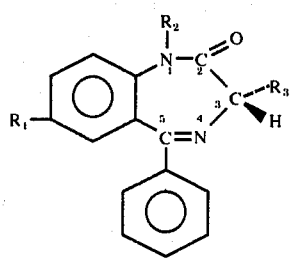

but solely in the form of racemates have been disclosed in J. Org. Chem. 27 3781 and 3788 (1963), Reeder et al, U.S. Pat. No. 3,371,085, and Japanese Patent 44/26302. These racemates are known to have sedative and tranquilizing effects.

However, the receptor theory of drug action, which teaches that pharmacologically active compounds act by interaction with a receptor which is a part of the cell affected by the action of a drug and is probably situated on the surface of the cell membrane, suggests that the racemic mixtures of compounds might not be as effective as a particular one of the optical isomers making up the racemic mixture.

According to the receptor theory of drug activity, the receptors are probably side chains or parts of the macromolecules which make up the cell surface layer. These side chains or parts of molecules have a definite, three-dimensional configuration, and can thus interact only with molecules possessing a complementary configuration. It is known that a relatively minor change in molecular shape can greatly alter the physiological effects of a chemical compound. This may be due to a change in the ability of the particular compound to bind itself to a particular receptor.

Indeed, there are cases known in which the S- and R-forms of optically active pharmacologically effective compounds are known to have different pharmacological effects. It cannot be predicted whether the enantiomers of optically active pharmacologically active compounds will have different effects in a given instance because the properties of the individual receptors are not known in detail, and the mechanisms by which pharmacologically active compounds exert their effects are also generally unknown. Nor can it be predicted which optical isomer will be active, nor how effective it will be in comparison to the optical isomer of opposite rotation or the racemic mixture. Of all presently known optically active drugs, the S- and R- configurations are found in almost equal numbers.

It is also very important to known what isomer is the active one in those cases where the enantiomers differ in effectiveness. Inactive forms dilute the active form, may be competitive antagonists, and may even have dangerous side effects. For example, the S- form of Ethambutole is an anti-tuberculous agent, while the R-form causes blindness in experimental animals, even at low dosages.

Therefore, one object of the present invention is to provide new optically active forms of 1–4 benzodiazepines.

Another object of the present invention is to provide a process for the preparation of solely a particular optically active form of 1–4 benzodiazepines.

A further object of the present invention is to provide compositions for administration of these useful compounds.

SUMMARY OF THE INVENTION

It has now been found that compounds of formula I

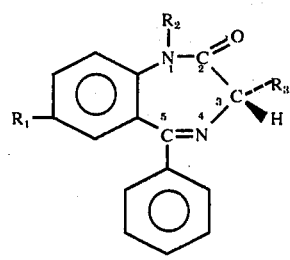

having an asymmetric carbon atom in position 3 wherein $R_1$ is hydrogen, halogen or a nitro or trifluoromethyl group, $R_2$ is hydrogen or $C_{1-4}$ lower alkyl and $R_3$ is $C_{1-4}$ lower alkyl, hydroxy $C_{1-4}$ lower alkyl phenyl, hydroxy phenyl, benzyl, hydroxy benzyl, or 3'-methyleneindolyl, can be prepared in the pure 3S form. These compounds have pharmacological activity affecting the central nervous system (CNS) as tranquilizers and have a surprisingly greater effectiveness than compounds of the same formula in the form of racemic mixtures.

It has now also been found that optically active compounds of formula I may be obtained according to the invention by reacting a compound of the formula

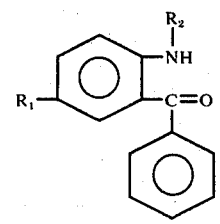

wherein $R_1$ and $R_2$ are as defined previously with a compound of formula

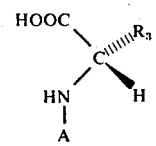

wherein $R_3$ is as defined previously and A is H.HCl, H.HBr tertbutoxycarbonyl (Boc), phthalimido, carbobenzoxy (Cbo), or other protective group, to form an intermediate compound having the formula

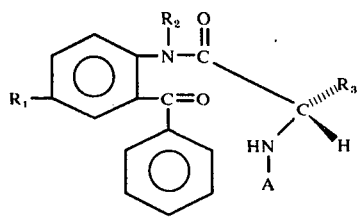

wherein $R_1$, $R_2$, $R_3$ and A are as defined previously.

The intermediate compounds of formula IV are also new compounds.

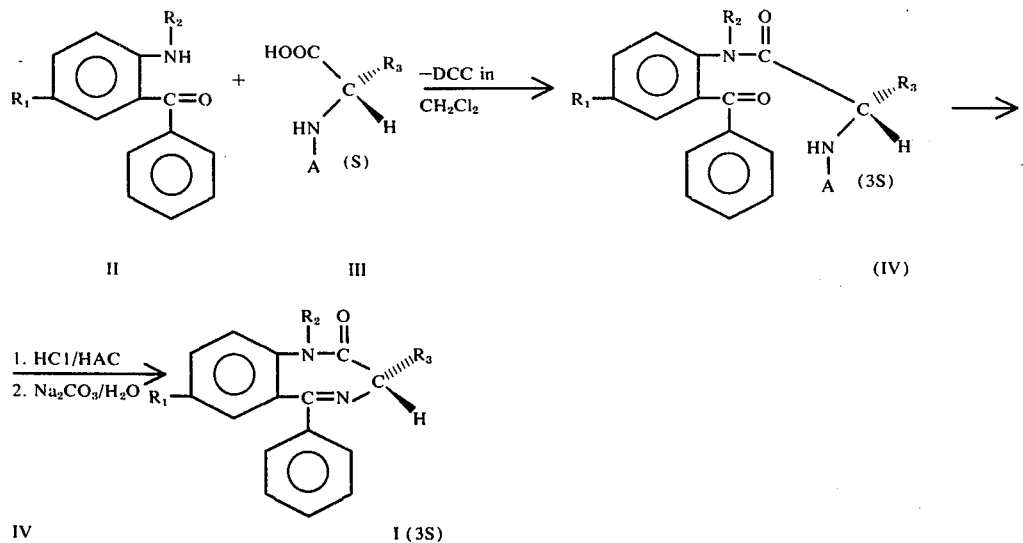

The protective group A of the compound of formula IV is removed to form a free amino group, which then reacts with the carbonyl group to form the compounds of formula I. According to the invention, the reaction between compounds II and III is carried out in an inert solvent and the elimination of protective group A from compounds of formula IV is accomplished by hydrolysis in an alkaline or acidic medium.

The optically active compounds of formula I according to this invention all occur in the 3S configuration and show a substantially higher pharmacological activity than the optically inactive racemic mixtures of the prior art. This may be explained since, as discussed above, where optically active compounds are concerned, often only one form is active in the human organism, while the other form is inactive. Each medicinal preparation affects, practically speaking, one enzymatic system which is substantially responsible for the resulting effect (as a result of the specific space orientation, these systems only react with compounds of a certain configuration). It can be assumed that just one form of the racemic compounds having the general formula I is biologically active, while the other form could be a strong antagonist. The elimination of the antagonistic form results in a multiple increase in the activity, since the antagonistic isomer no longer competes with the biologically active form (during the attachment to the receptor inside the CNS). As a result of this, the compounds according to the invention show at least a 3 to 4 times higher activity, in test animals, when compared with the corresponding racemates.

The prepared compounds are completely new and have not been described previously; as a result of this, the optically active 1,4-benzodiazepines have been synthesized for the first time by the process according to the present invention.

DESCRIPTION OF THE PREFERRED EMBODIMENTS

The preferred compounds according to this invention are those in which $R_1$ is chlorine, $R_2$ is hydrogen, and $R_3$ is selected from the group consisting of methyl, benzyl, p-hydroxy benzyl, and isopropyl.

The novel compounds of this invention are synthesized according to the following reaction scheme.

According to the above reaction scheme, a 2-aminobenzophenone (II) is reacted with an alpha-amino acid having a protected amino group (III) in an inert solvent in the presence of a suitable catalyst to form an intermediate benzophenone derivative (IV).

Preferred, novel intermediate compounds of formula IV are those in which $R_1$ is chlorine, $R_2$ is hydrogen, $R_3$ is selected from the group consisting of methyl, benzyl, p-hydroxy benzyl, and isopropyl and A is selected from the group consisting of cabobenzoxy, t-butoxy carbonyl, and H.HBr.

Suitable inert solvents are those which will not cause the optically active amino acid derivative or the intermediate optically active benzophenone derivative to become racemized. Examples of such solvents are methylene chloride and tetrahydrofuran (THF). The catalyst used in the reaction of the 2-amino benzophenone with the alpha-amino acid derivative may be any suitable catalyst which does not cause racemization of the alpha-amino acid or the intermediate product. A preferred catalyst is dicyclohexylcarbodiimide (DCC).

A preferred 2-amino-benzophenones is 2-amino-5-chlorobenzophenone.

Preferred alpha-amino acids having a protective group on the amino group are the Boc-and Cbo-protected alpha-amino acids having the 3S configuration. Examples of such alpha-amino acids are N-Boc- and N-Cbo- derivatives of L-alanine, L-valine, L-threonine, L-phenylalanine, L-tyrosine, and L-tryptophane.

Representative intermediate compounds of formula IV having a Boc or Cbo protective group are listed in Table I.

Intermediate compounds of formula IV having a Boc or Cbo protective group may be further converted to an intermediate compound having formula IV wherein group A is H.HCl or H.BRr. These further intermediate compounds may be isolated and characterized. Representative intermediate compounds having formula IV of this type are listed in Table II.

The Boc and Cbo protective groups may be removed by hydrolysis or hydrogenolysis. The hydrolysis is conveniently carried out using a 3% solution of hydrobromic or hydrochloric acid in glacial acetic acid (HAC) when the protective group is Cbo. However, 48% hydrobromic acid is glacial acetic acid can also be used. The Cbo group may also be removed by hydrogenolysis in a suitable inert solvent using 10% palladium supported on carbon as a catalyst. The Boc group is preferably removed with glacial acetic acid or a mixture of glacial acetic acid containing concentrated hydrochloric acid.

After the protective group has been removed, the intermediate compound may be isolated as the acid salt (compound of formula IV wherein group A is, for example H.HBr) or the free base by conventional procedures of extraction and crystallization and subsequently cyclized, or the amino compound may be cyclized in basic solution without isolation in crystalline form. The cyclization takes place in an inert solvent under mildly basic conditions and at a relatively low temperature. The mild conditions are used to prevent racemization of the intermediate compound or product. Inert solvents are those which do not cause racemization of the intermediarte or product. Organic, aqueous, and aqueous-organic solvents may be used. Examples of suitable solvents include water and methanol-water (1:1) mixtures and dioxane-ethanol mixtures. Likewise, the temperature used for the cyclization reaction should be low enough to avoid racemization, and preferably no higher than 40° C.

When the Boc or Cbo protective group is removed by hydrogenolysis in a suitable inert solvent, the cyclization may take place concurrently with the hydrogenolysis. In this way, the removal of the protective group and cyclization can be carried out in a single step.

The pharmacalogical activity of the novel compounds of this invention was evaluated by standard methods such as the anticonvulsant effect against pentylene tetrazole shock and maximal and minimal electroshock, muscle relaxing ability, the fighting test, and hypnotic effect. These standard test are described in detail in the literature, for example, in L. O. Randall, C. L. Schenkel, R. F. Banziger, *Curr. Ther. Res., Clin. Exp.*, 590 (1965), and M. I. Gluckman, *Curr. Ther. Res., Clin. Exp.*, 7,721 (1965).

The novel compounds of this invention were found to have substantially higher pharmacalogical activity than the corresponding racemic mixtures.

The compounds of this invention may be administered in pharmaceutical compositions in combination with any suitable pharmaceutical vehicle. Thus, they may be administered as solutions, in capsules, tablets, and the like. Suitable formulations for pharmaceutical preparations containing the customary vehicles, adjuvants, and the like, may be taken from standard pharmaceutical reference works such as the U.S. Pharmacopoeia.

The following examples will illustrate the practice of this invention, but are not intended to limit its scope.

In these examples all melting points were determined on a Kofler-Mikroheiztish, and are uncorrected. Ir spectra were obtained on a Perkin Elmer Model 131 Spectrophotometer; uv spectra measurements were performed on a Zeiss Opton PMQ II Spectrophotometer; nmr spectra were obtained on a Varian A-60 or Varian T-60 apparatus using TMS (0.00 Hz) or Silicone grease (4.0 Hz) as internal standard. Rotations were measured on a Perkin Elmer Model 141 apparatus. Thin-layer and column chromatography were performed with the materials and by methods described in V. Sunjic, F. Kajfez, D. Kolbah and N. Blazevic, *Croat. Chem. Acta*, 43,205 (1971). Light petroleum refers to the fraction b.p. 40°-60°.

The novel optically active compounds of formula I may also be prepared by the method described in Assignees' copending application by Kajfez, U.S. Ser. No. 492,912 filed July 29, 1974.

Examples 1 through 9 illustrate the synthesis of intermediate compounds of formula IV according to the invention, wherein $R_1$=Cl, $R_2$=H, and $R_3$ is varied. The yield of each synthesis, the melting point of the product, the optical rotation [$\alpha$] at wavelengths of 578 and 546 nanometers (with solvents and concentrations), and the elemental analyses are tabulated in Table I.

EXAMPLE 1

In 20 ml of methylene chloride 5.08 g (22.0 mmoles) of 2-amino-5-chloro-benzophenone and 20.0 mmoles of N-Boc-L-alanine were dissolved. Dicyclo-hexylcarbodiimide (DCC) (4.49 g, 22.0 mmoles) dissolved in 20 ml of methylene chloride was added to this solution, dropwise during 1 hour at 0° C and with stirring. After additional stirring at room temperature for 8 hours, the dicyclohexylurea formed was suctioned off and the filtrate evaporated to dryness. The residual crude product was recrystallized from cyclohexane to give 6.95 g of the compound of formula IV having $R_1$=Cl, $R_2$=H, $R_3$=CH and A=Boc. The crude melting point was 150° C–154° C. Two further recrystallizations from the same solvent gave the analytically pure sample, m.p. 154°–155° C.

EXAMPLE 2

By the procedure of Example 1 except that N-Boc-L-phenylalanine was used in place of N-Boc-L-alanine, the crude compound of formula IV wherein $R_1$=Cl, $R_2$=H, $R_3$=CH$_3$-C$_6$H$_5$ was prepared. The crude compound was purified by column chromatography (320 g of silica gel, ether-methylene chloride 1:1 as eluent). Fractions of 10 ml each were collected and fractions 11–27 gave 7.50 g of the compound of formula IV wherein $R_1$=Cl, $R_2$=H, $R_3$=CH$_2$-C$_6$H$_5$, m.p. 132°–137°C. Recrystallization from cyclohexane gave the analytically pure sample, m.p. 137°–139° C.

EXAMPLE 3

By the procedure of Example 1, except that N-Boc-L-tyrosine was used in place of N-Boc-L-alanine and 30 ml of dried tetrahydrofuran was used in place of the methylene chloride solvent, the crude compound of formula IV wherein $R_1$=Cl, $R_2$=H, and $R_3$=p-hydroxybenzyl was prepared. The crude product was purified by recrystallization from cyclohexane (900 ml). The compound crystallized as a voluminous precipitate which was filtered off with difficulty, m.p. 150°–156° C.

An analytically pure sample 158°-obtained by column chromatography (ether as eluent), m.p. 158°-160° C.

EXAMPLE 4

By the reaction procedure of Example 3, except that N-Boc-L-tryptophane was used in place of N-Boc-L-tyrosine, a reaction mixture containing the crude compound of formula IV wherein $R_1$=Cl, $R_2$=H, $R_3$=3'-methyleneindolyl, and A=Boc was prepared. The crude product was separated from the reaction mixture by column chromatography (360 g of silica gel, methylene chloride-ether 10:1 as eluent). Fractions having a volume of 30 ml each were collected, and fractions 24–37 gave 6.52 g of the chromatographically pure compound. Recrystallization from benzene-light petroleum gave the pure sample with m.p. 152°–154° C.

EXAMPLE 5

By the reaction procedure of Example 3, except that N-Boc-L-threonine was used in place of N-Boc-tyrosine, a reaction mixture containing the crude compound of formula IV wherein $R_1$=CL, $R_2$=H, $R_3$=threnyl, and A=Boc was prepared. The reaction mixture was then subjected to column chromatography on a column of 300 g of silica gel. Elution with 500 ml of methylene chloride gave 4.12 g of starting 2-amino-5-chlorobenzophenone and DCC. Thereafter, a mixture of methylene chloride-ether (4:1) was used, and 7.2 grams of the crude compound were obtained. After recrystallization from ether-light petroleum, the pure sample melted at 67°–70° C.

EXAMPLE 7

Starting with 33.5 g (0.15 mole) of N-Cbo-L-alanine, 27.7 g (0.12 mole) of 2-amino-5-chlorobenzophenone and 30.7 g (0.15 mole) of DCC the same general reaction procedure as in Example 1 was followed and the crude compound of formula IV wherein $R_1$=Cl, $R_2$=H, $R_3$=methyl, and A=Cbo was obtained by crystallization from 210 ml of hot cyclohexane, m.p. 144°–147° C.

EXAMPLE 8

By the procedure of Example 7, except that N-Cbo-L-phenylalanine (45.0 g, 0.15 mole) was used in place of N-Cbo-L-alanine and the crude product was recrystallized from cyclohexane-ether (20:1) instead of cyclohexane; the compound of formula IV wherein $R_1$=Cl, $R_2$=H, $R_3$=benzyl and A=Cbo was prepared.

EXAMPLE 9

31.5 g (0.10 mole) of N-Cbo-L-tyrosine, 0.10 mole of DCC, and 0.09 mole of 2-amino-5-chlorobenzophenone were reacted by the general procedure of Example 1 using absolute T H F as a solvent instead of methylene chloride. The compound of formula IV wherein $R_1$=Cl, $R_2$=H, $R_3$=p-hydroxybenzyl, and A=Cbo was isolated from the crude reaction mixture by column chromatography (600 g of silica gel). By elution with methylene chloride (150 ml) unconverted amine and DCC were separated. Elution with methylene chloride-ether (5:1) gave the crude product which recrystallized from cyclohexane-ether (10:1), m.p. 117°–120° C.

TABLE I

| | | | | | | | Elemental Analysis | | | | | |
|---|---|---|---|---|---|---|---|---|---|---|---|---|
| | | | | | | | | Calcd. | | | Found | |
| Ex. | $R_3$ | A | Yield % | M.p.° C | $[\alpha]578[\alpha]546$ | Formula | C | % H | N | C | % H | N |
| 1 | —$CH_3$ | Boc | 86.4 | 154–155 | −58.5° −68.0° | $C_{21}H_{23}ClN_2O_4$ | 62.61 | 5.75 | 6.95 | 62.48 | 5.71 | 6.7 |
| 2 | —$CH_2$—$C_6H_5$ | Boc | 78.5 | 137.5–139 | −72.0° −85.1° 1.196/$CHCl_3$ | $C_{27}H_{27}ClN_2O_4$ | 67.70 | 5.68 | 5.85 | 67.71 | 5.73 | 5.85 |
| 3 | —$CH_2$—$C_6H_5$—p-OH | Boc | 61.2 | 158–160 | −66.9° −79.2° 0.688/$CHCl_3$ | $C_{27}H_{27}ClN_2O_5$ | 64.93 | 5.82 | 5.24 | 64.70 | 5.62 | 5.41 |
| 4 | —$CH_2$—3'-indolyl | Boc | 51.5 | 152–154 | −89.5° −106° 1.314/$CHCl_3$ | $C_{29}H_{28}ClN_3O_4$ | 67.24 | 5.45 | 8.12 | 67.30 | 5.21 | 7.99 |
| 5 | —CHOH—$CH_3$ | Boc | 47.5 | 79–81 | −39.6° −69.0° 1.020/$CHCl_3$ | $C_{22}H_{25}ClN_2O_5$ | 61.05 | 5.82 | 6.47 | 60.94 | 5.56 | 6.34 |
| 6 | —CH($CH_3$)$_2$ | Boc | 59.0 | 106–108 | −48.3° −57.2° 1.118/$CHCl_3$ | $C_{23}H_{27}ClN_2O_4$ | 64.12 | 6.30 | 6.49 | 63.90 | 6.60 | 6.25 |
| 7 | —$CH_3$ | Cbo | 82.5 | 117–119 | −17.8° −22.0° 2.180/$CHCl_3$ | $C_{24}H_{21}ClN_2O_4$ | 65.99 | 4.84 | 6.41 | 66.31 | 5.14 | 6.40 |
| 8 | —$CH_2$—$C_6H_5$ | Cbo | 66.0 | 115–116 | −48.5° −55.8° 1.200/$CHCl_3$ | $C_{30}H_{25}ClN_2O_4$ | 70.24 | 4.91 | 5.46 | 69.90 | 4.92 | 5.24 |
| 9 | —$CH_2$—$C_6H_4$—p-OH | Cbo | 57.5 | 117–120 | −33.1° −39.3° 0.968/$Me_2CO$ | $C_{30}H_{25}ClN_2O_5$ | 68.12 | 4.76 | 5.30 | 67.91 | 4.49 | 5.17 |

EXAMPLE 6

By the reaction procedure of Example 1, except that N-Boc-L-valine was used in place of N-Boc-L-alanine, the reaction mixture containing the crude compound of formula IV wherein $R_1$=Cl, $R_2$=H, $R_3$=isopropyl, and A=Boc was prepared. The crude reaction mixture was applied to a column containing 350 g of silica gel. By elution with methylene chloride (500 ml), 4.05 g of a mixture of starting 2-amino-5-chlorobenzophenone and DCC was separated. Elution with methylene chloride-ether (10:1) gave 6.4 g of the mixture of the crude compound and by-products. This mixture was separated on a second column (220 g of silica gel, light petroleum-methylene chloride-ether, 10:5:1, as eluent). There was obtained 5.08 g of the chromatographically pure compound as a viscous oil which after crystallization from cyclohexane had a m.p. 106°–108° C.

Examples 10 through 15 illustrate the synthesis of other intermediate compounds having formula IV wherein the Boc or Cbo protective group has been removed by hydrolysis and replaced by H.HBr. These novel intermediates are listed in Table II together with their melting points and their optical rotations [α] at wavelengths of 578 and 546 nanometers at given concentrations in the given solvents.

EXAMPLE 10

0.1 moles of (+)-S-)S-5-chloro-2-(carbobenzoxyalanyl)-amino-benzophenone (compound of formula IV wherein $R_1$=Cl, $R_2$=H, $R_3$=methyl, and A=Cbo) was dissolved in 120 milliliters of 4 molar HBR/$CH_3$COOH while being cooled in an ice bath. After 10 minutes the ice bath was removed and the reaction mixture was allowed to warm to room temperature. The mixture was then stirred until evolution of gas from the solution ceased. The reaction mixture was evaporated to dryness in a rotary evaporator and then with the addition of three 200 milliliter portions of benzene and subsequent evaporation was again dried. The oily residue was crystallized by addition of ether. The crude product was recrystallized from ether-methanol, with the addition of some cyclohexane.

The product was the compound of formula IV wherein $R_1$=Cl, $R_2$=H, $R_3$=methyl and A=H.HBr.

EXAMPLES 11–15

By the procedure of Example 10, starting with the appropriately substituted compound of formula IV in which A=Cbo the corresponding compounds having A=H.HBr and $R_1$, $R_2$ and $R_3$ as specified in Table II were prepared.

Examples 16 through 19 illustrate the synthesis of intermediate compounds having formula IV wherein A=H.HBr by hydrogenolysis of the compounds of formula IV wherein A=Cbo. These novel intermediates are listed in Table II along with the compounds prepared in Examples 10–15.

EXAMPLE 16

0.1 moles of (+)-S-5-chloro-2-(N-methyl-N-carbobenzoxyalanyl)-amino-benzophenone (compound having formula IV wherein $R_1$ = Cl, $R_2$ = methyl, $R_3$ = methyl, A = Cbo) was dissolved in 150 milliliters of 90% methanol and added to 0.2 to 0.3 moles HBr/$CH_3$COOH and 10% Pd-C in a quantity equivalent to 10% of the added material. Then a hydrogenation was carried out in a closed system without significant excess pressure. The course of the reaction was followed by thin layer chromatography until the disappearance of the spot of starting material (ether-chloroform was used as the solution solvent). After the conclusion of the reaction, the catalyst was filtered off and the reaction mixture was evaporated to dryness. The residue was worked up in the same fashion as described in Example 10.

EXAMPLES 17–19

By the procedure of Example 16, starting with appropriately substituted compound of formula IV in which A = Cbo the corresponding compounds having A = H.HBr and $R_1$, $R_2$, and $R_3$ as specified in Table II were prepared.

TABLE II

| Ex. | $R_1$ | $R_2$ | $R_3$ | M.P. °C | $[\alpha]$ 578<br>$[\alpha]$ 546<br>c (in $CHCl_3$) |
|---|---|---|---|---|---|
| 10 | Cl | H | —$CH_3$ | 129–131 | −66.7°<br>−80.4°<br>2.364 in $H_2O$ |
| 11 | Cl | H | 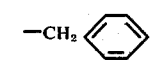 | 240–245 | −41.3°<br>−51.1°<br>1.211 in MeOH |
| 12 | Cl | H | 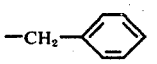 | 160–165 | −38.5°<br>−45.8°<br>1.586 in MeOH |
| 13 | Cl | H | 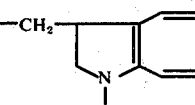 | 237–240 | + 9.4°<br>+ 2.65°<br>0.748 in MeOH |
| 14 | Cl | H | 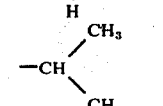 | 240–243 | −17.1°<br>−21.7°<br>0.760 in MeOH |
| 15 | Cl | H | 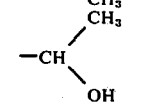 | 112–115 | − 4.8°<br>−11.20°<br>0.624 in MeOH |
| 16 | Cl | $CH_3$ | —$CH_3$ | 165–167 | −60.2°<br>−83.5°<br>2.403 in MeOH |
| 17 | $NO_2$ | H | —$CH_3$ | 172–174 | + 9.3°<br>−36.3°<br>1.385 in MeOH |
| 18 | H | $CH_3$ | 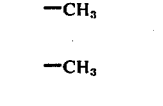 | 248–250 | −48.2°<br>−56.2°<br>1.354 in |
| 19 | $CF_3$ | H | —$CH_3$ | 158–160 | −35.7°<br>−56.2°<br>1.453 in MeOH |

EXAMPLE 20

A. 8.55 g of the compound of formula IV wherein $R_1$ = Cl, $R_2$ = H, $R_3$ = $CH_3$ and A = Boc were dissolved in 45 ml of acetic acid at 0° C and 5 ml of hydrogen bromide - acetic acid (4M) was added dropwise. After 5 minutes 50 ml of benzene was added and the reaction mixture evaporated in vacuo. The residual oil was dissolved in 200 ml of ethanol-water (1:1) and the pH adjusted to 8.5 by addition of 5% sodium hydroxide. After stirring overnight at room temperature (not over 25° C) the solution was partially evaporated in vacuo, 300 ml of water was added and the mixture extracted with 3 × 100 ml of methylene chloride. The organic layer was dried (sodium sulfate), evaporated, and the residual oil recrystallized from 150 ml of acetone-water (1:1). The pure product (compound of formula I wherein $R_1$ = Cl, $R_2$ = H and $R_3$ = $CH_3$) was recrystallized and melted at 200°–203° C. nmr ($CDCl_3$): 1.76 ppm (d, 3H), 3.79 (qv. 1H), 7.3–7.8 (m, 1H), 9.25 (s, 1H). Analysis: calculated for $C_{16}H_{13}ClN_2O$ (284.74):

C, 67.49; H, 4.61, N, 9.84. Found C, 67.21; H, 4.88; N, 9.54.

B. 21.75 g (0.05 mole) of compound of the formula IV wherein $R_1$ - Cl, $R_2$ = H, $R_3$ = $CH_3$ and A = Cbo were dissolved in 150 ml of a mixture of dioxane and ethanol (2:1) and 2.0g 10% Pd - C were added. Flow hydrogenation was performed during 6 hours after which time no starting material was present and thin-layer chromotography indicated that about 80% of the free amine had cyclized. The catalyst was filtered off, the filtrate was evaporated in vacuo and the residual oil was recrystallized, yielding 12.8 g of the compound of formula I wherein $R_1$ = Cl, $R_2$ = H, $R_3$ = $CH_3$, having the same physical constants as the compound prepared by method A.

EXAMPLE 21

By the method of Example 20B except that the compound of formula IV having $R_1$ = Cl, $R_2$ = H, $R_3$ = benzyl, A = Cbo was used as the starting material the compound of formula I having $R_1$ = Cl, $R_2$ = H and $R_3$ = benzyl was prepared.

EXAMPLE 22

By the procedure of Example 20A except that the compound of formula IV wherein $R_1$ = $CH_3$, $R_2$ = H, $R_3$ = p-hydroxybenzyl, and A = Cbo was used as the starting material, the compound of formula I wherein $R_1$ = Cl, $R_2$ = H, and $R_3$ = p-hydroxybenzyl was prepared. The crude product was purified by column chromatography (ether-petroleum ether, 3:1 as eluent) followed by recrystallization from ether-cyclohexane.

EXAMPLE 23

By the procedure of Example 20A, except that the compound of formula IV wherein $R_1$ = Cl, $R_2$ = H, $R_3$ = 3'-methyleneindolyl and A = Boc was used as the starting material, the compound of formula I wherein $R_1$ = Cl, $R_2$ = H, and $R_3$ = 3'-methyleneindolyl was prepared. The product was recrystallized from ether. One mole of ether included in the crystallized product could not be removed even after prolonged drying at 80° C and 0.01 mm of mercury over phosphorus pentoxide.

EXAMPLE 24

By the procedure of Example 20A, except that the compound of formula IV wherein $R_1$ = Cl, $R_2$ = H, $R_3$ = 1'-hydroxyethyl, and A = Boc was used as starting material, the compound of formula I wherein $R_1$ = Cl, $R_2$ = H, and $R_3$ = 1'-hydroxyethyl was prepared. The compound was purified by column chromatography (petroleum ether-methylene chloride - ether, 1:2:4 as eluent).

EXAMPLE 25

By the procedure of Example 20A, except that the compound of formula IV having $R_1$ = Cl, $R_2$ = H, $R_3$ = isopropyl and A = Boc was used as the starting material, the compound of formula I wherein $R_1$ = Cl, $R_2$ = H, and $R_3$ = isopropyl was prepared. The compound was recrystallized from petroleum ether -methylene chloride (40:1).

EXAMPLE 26

10.0 g of the compound of formula I wherein $R_1$ = Cl, $R_2$ = H, and $R_3$ = $CH_3$ were dissolved in 40 ml of dimethyl formamide (DMF) under nitrogen. Anhydrous barium oxide (2.0 g) was added and 3 ml of methyl iodide diluted in 10 ml of DMF was added dropwise with stirring during 0.5 hour. After 6 hours stirring the reaction mixture was diluted with 500 ml of water and extracted with three 200 ml portions of methylene chloride. The organic layer was dried (magnesium sulfate) and evaporated. The residual oil was applied to a column (300 g of silica gel) and eluted with methylene chloride (pure) to remove free 2-amino-5-chlorobenzophenone. Elution with ether-methylene chloride gave the compound of formula I wherein $R_1$ = Cl, $R_2$ = $CH_3$, and $R_3$ = $CH_3$ as a viscous oil. The compound was recrystallized from light petroleum.

EXAMPLE 27

By the procedure of Example 26, except that the compound of formula I wherein $R_1$ = Cl, $R_2$ = H, and $R_3$ = benzyl was used as the starting material, the compound of formula I wherein $R_1$ = Cl, $R_2$ = $CH_3$ and $R_3$ = benzyl was prepared. The compound was recrystallized from light petroleum.

EXAMPLE 28

0.05 moles of the compound of formula IV in which $R_1$ = $NO_2$, $R_2$ = H, $R_3$ = methyl and A = H.HBr were dissolved in a mixture of water-ethanol (100 ml:100 ml). 10% sodium hydroxide solution was added until the pH was 8.5 and the mixture was stirred at room temperature or on a water bath at 40° C. The ensuing cyclization reaction was followed by thin layer chromatography (ether-$CHCl_3$ (1:1) as eluting solvent). After the conclusion of the reaction of the solvent mixture was evaporated in a rotary evaporator and the residue was crystallized from acetone-water solvent mixture.

EXAMPLES 29–31

By the process of Example 28 starting from the appropriately substituted compound of formula IV the compounds of formula I listed in Table III were prepared.

EXAMPLE 32

This Example illustrates the pharmacological effectiveness of the compounds of this invention. A number of the compounds of this invention were tested for their pharmacological effect on the CNS by the procedures described above. Also tested were the corresponding racemic mixtures and three commercial tranquillizers:
 Diazepam = 7-chloro-1,3-dihydro-1-methyl-5-phenyl-2H-1,4-benzodiazepine-2-one ("Valium"),
 Medazepam = 7-chloro-5-phenyl-1-methyl-1,2-dihydro-3H-1,4-benzodiazepine
 Oxazepam = 7-chloro-1,3-dihydro-3-hydroxy-5-phenyl-2H-1,4-benzodiazepine-2-one The results of the tests are shown in Table IV wherein the relative potencies compared with that of chlordiazepoxide which is assigned an activity of 1.00. The larger the numerical values, the less effective is the tranquillizing power in the given test. From the results presented in Table V, it can be seen that the racemic mixtures are typically 6–10 times less effective than the pure optical isomers of this invention. It can also be seen that the pharmaceutically active compounds of this invention compare favorably with some commercially useful tranquillizers and even surpass them in some respects.

TABLE III

| Ex. | R₁ | R₂ | R₃ | MP °C | [α] 578 [α] 546 c (in CHCl₃) |
|---|---|---|---|---|---|
| 20 | Cl | H | —CH₃ | 200–203 | +172.5° +201° 2.492 |
| 21 | Cl | H | —CH₂—C₆H₅ | 108–110 | +51.8° +58.4° 0.520 |
| 22 | Cl | H | —CH₂—C₆H₄—OH | 139–141 | +42.5° +502° 0.600 |
| 23 | Cl | H | —CH₂-(indole) | 150–152 | +40.4° +48.3° 1.068 |
| 24 | Cl | H | —CHOH—CH₃ | 118–121 | +154° +179° 1.088 |
| 25 | Cl | H | —CH(CH₃)₂ | 192–194 | +148° +171° 1.116 |
| 26 | Cl | CH₃ | —CH₃ | 47–50 | +212° +249° 0.852 |
| 27 | Cl | CH₃ | —CH₂—C₆H₅ | 135–137 | +98.9° +116.0° 1.388 |
| 28 | NO₂ | H | —CH₃ | 96–98 | +132.5° +177° 0.674 |
| 29 | H | CH₃ | —CH₂—C₆H₅ | 135–137 | +98.9° +116° 1.388 |
| 30 | CF₃ | H | —CH₃ | 87–90 | +74.6° +99.8° 0.892 |
| 31 | Cl | CH₃ | —O—CH₂CHOHCH₂OH | | |

TABLE IV

Pharmacological potencies of Benzodiazepines in various tests in mice
(Relative Potencies in Comparison with Chlordiazepoxide)

| Compound of Example | Anticonvulsant effect | | | Muscle relaxation | Fighting test | Hypnotic effect | LD 50 P.O. |
|---|---|---|---|---|---|---|---|
| | Pentylene tetrazole | Maximal electro shock | Minimal electro shock | | | | |
| 20 (S) | 4.1 | 1.32 | 0.20 | 1.0 | 1.0 | 0.4 | 2300 |
| 20 (Rac.) | 30.40 | 8.20 | 5.00 | 9.60 | 10.4 | 2.30 | |
| 21 (S) | 5.30 | 4.82 | 2.30 | 4.10 | 4.50 | 2.10 | 1600 |
| 21 (Rac.) | 40.50 | 10.30 | 20.60 | 40.70 | 45.8 | 10.70 | |
| 22 (S) | 7.3 | 6.30 | 1.42 | 4.30 | 5.70 | 4.20 | 1850 |
| 22 (Rac.) | 75.6 | 65.40 | 16.70 | 46.20 | 56.30 | 18.60 | |
| 23 (S) | 3.20 | 4.10 | 1.70 | 6.20 | 7.10 | 0.80 | 2300 |
| 23 (Rac.) | 30.60 | 38.70 | 14.60 | 60.50 | 80.30 | 8.30 | |
| 24 (S) | 10.30 | 1.30 | 0.45 | 0.62 | 1.70 | 0.51 | 6000 |
| 24 (Rac.) | 105.60 | 12.60 | 3.27 | 5.42 | 16.30 | 3.20 | |
| 25 (S) | 1.80 | 1.75 | 0.30 | 1.15 | 1.40 | 0.80 | 1850 |
| 25 (Rac.) | 20.4 | 20.30 | 4.70 | 8.60 | 9.30 | 4.20 | |
| 26 (S) | 5.80 | 0.90 | 0.10 | 0.70 | 1.00 | 0.80 | 2600 |
| 26 (Rac.) | 47.30 | 10.20 | 2.10 | 6.54 | 8.94 | 2.70 | |
| 31 (S) | 10.30 | 0.38 | 0 | 0.80 | 1.0 | 0.42 | 6000 |
| 31 (Rac.) | 105.4 | 4.72 | 2.30 | 9.60 | 8.74 | 2.30 | |
| Diazepam | 6.7 | 5.20 | 1.73 | 3.30 | 4.3 | 1.75 | 800 |
| Medazepam | 6.2 | 1.03 | 0.32 | 1.3 | 1.0 | 0.30 | 1420 |
| Oxazepam | 12.3 | 2.1 | 0.77 | 0.62 | 1.3 | 0.48 | 3700 |

We claim:
1. An optically active compound having the formula

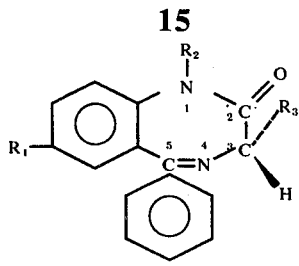

having an asymmetric carbon atom in position 3, said asymmetric carbon atom having the S configuration, wherein $R_1$ is selected from the group consisting of hydrogen, halogen, nitro, and trifluoromethyl, $R_2$ is selected from the group consisting of hydrogen and $C_{1-4}$ lower alkyl and $R_3$ is selected from the group consisting of $C_{1-4}$ lower alkyl, hydroxy-$C_{1-4}$ lower alkyl phenyl, hydroxy phenyl, benzyl, hydroxy benzyl, and 3'-methyleneindolyl.

2. A compound according to claim 1 wherein $R_1 =$ Cl, $R_2 =$ H and $R_3 =$ $CH_3$.

3. A compound according to claim 1 wherein $R_1 =$ Cl, $R_2 =$ H and $R_3 =$

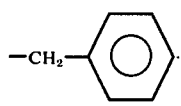

4. A compound according to claim 1 wherein $R_1 =$ Cl, $R_2 =$ H and $R_3 =$

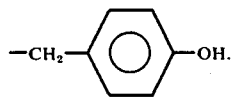

5. A compound according to claim 1 wherein $R_2 =$ $CH_3$.

6. A process for preparing an optically active compound having the formula

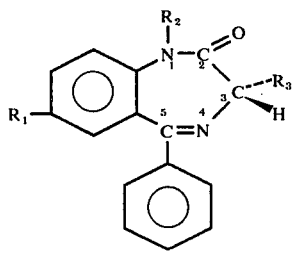

having an asymmetric carbon atom in position 3 said asymmetric carbon atom having the S configuration wherein $R_1$ is selected from the group consisting of hydrogen, halogen, nitro, and trifluoromethyl, $R_2$ is selected from the group consisting of hydrogen and $C_{1-4}$ lower alkyl, and $R_3$ is selected from the group consisting of $C_{1-4}$ lower alkyl, hydroxy $C_{1-4}$ lower alkyl, phenyl, hydroxy phenyl, benzyl, hydroxy benzyl, and 3'-methyleneindolyl, comprising the steps of a. reacting a compound having the formula

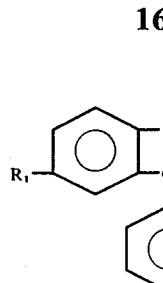

wherein $R_1$ and $R_2$ have the same meaning as was defined in formula I, in an inert solvent, selected from the group consisting of methylene chloride, tetrahydrofuran and mixtures thereof with a compound having the formula

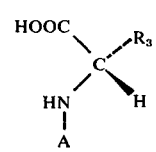

in the presence of dicyclohexylcarbodiimide and wherein $R_3$ has the same meaning as for the compound having formula I, and A is a protective group selected from the group consisting of carbobenzoxy and t-butoxy carbonyl, to form an intermediate compound having the formula

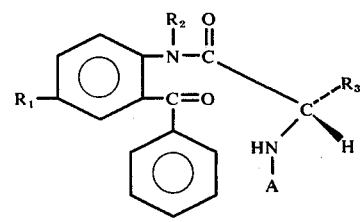

b. removing said protective group by acidic hydrolysis by treatment with HBr in acetic acid, HBr in methanol or mixture of 1:1 acetic acid in ethanol in an inert solvent at a temperature no greater than about room temperature, and c. cyclizing the compound of formula IV having its protective group removed in an inert solvent selected from the group consisting of water, a methanol-water mixture and the ethanol-water mixture at a pH of about 8.5 at a temperature no greater than about 40° C.

7. A process according to claim 6 wherein said inert solvent in step (a) is methylene chloride.

8. A process according to claim 6 wherein said acidic hydrolysis is carried out in glacial acetic acid solvent.

9. A process according to claim 6 wherein said inert solvent in step (c) is water.

10. A process according to claim 6 wherein said inert solvent in step (c) is a methanol-water mixture.

11. A process for preparing an optically active compound having the formula

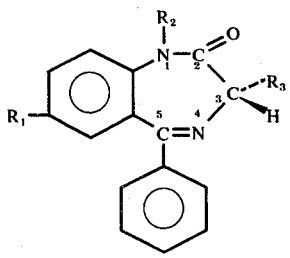

I having an asymmetric carbon atom in position 3 said asymmetric carbon atom having the S configuration wherein $R_1$ is selected from the group consisting of hydrogen, halogen, nitro, and trifluoromethyl, $R_2$ is selected from the group consisting of hydrogen and $C_{1-4}$ lower alkyl and $R_3$ is selected from the group consisting of $C_{1-4}$ lower alkyl, hydroxy $C_{1-4}$ lower alkyl, phenyl, hydroxy phenyl, benzyl, hydroxy benzyl and 3'-methyleneindolyl, comprising the steps of a. reacting a compound having the formula

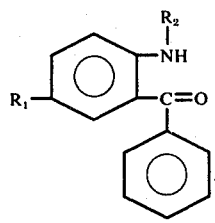

II wherein $R_1$ and $R_2$ have the same meaning as was defined in formula I, in an inert solvent, selected from the group consisting of methylene chloride, tetrahydrofuran and mixtures thereof with a compound having the formula

III in the presence of dicyclohexylcarbodiimide and wherein $R_3$ has the same meaning as for the compound having formula I, and A is a protective group selected from the group consisting of carbobenzoxy and t-butoxy carbonyl, to form an intermediate compound having the formula

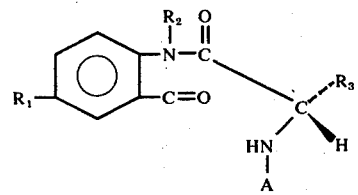

IV b. removing the protective group by catalytic hydrogenolysis in an inert solvent selected from aqueous methanol and dioxane: ethanol mixture at a temperature no greater than room temperature, and c. cyclizing the compound of formula IV having its protective group removed in an inert solvent at a pH of about 8.5 at a temperature no greater than about 40° C.

12. A process according to claim 11 wherein said inert solvent in step (a) is methylene chloride.

13. A process according to claim 11 wherein said catalytic hydrogenolysis is carried out in a solvent mixture consisting of hydrogenolysis is carried out in a dioxane-ethanol solvent mixture using a palladium catalyst supported on carbon.

14. A process according to claim 11 wherein said inert solvent in step (c) is water.

15. A process according to claim 11 wherein said inert solvent in step (c) is a methanol-water mixture.

* * * * *